(12) United States Patent
Homma et al.

(10) Patent No.: US 12,158,459 B2
(45) Date of Patent: Dec. 3, 2024

(54) HYDROGEN SENSOR, HYDROGEN DETECTION METHOD, AND HYDROGEN DETECTION DEVICE

(71) Applicant: Nuvoton Technology Corporation Japan, Kyoto (JP)

(72) Inventors: Kazunari Homma, Gifu (JP); Koji Katayama, Nara (JP); Ken Kawai, Osaka (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 272 days.

(21) Appl. No.: 17/957,686

(22) Filed: Sep. 30, 2022

(65) Prior Publication Data
US 2023/0022428 A1  Jan. 26, 2023

Related U.S. Application Data

(63) Continuation of application No. PCT/JP2021/014645, filed on Apr. 6, 2021.

(30) Foreign Application Priority Data

Apr. 16, 2020 (JP) .................... 2020-073461

(51) Int. Cl.
*G01N 33/00* (2006.01)
*G01N 27/12* (2006.01)

(52) U.S. Cl.
CPC ......... *G01N 33/005* (2013.01); *G01N 27/125* (2013.01)

(58) Field of Classification Search
CPC .................... G01N 33/005; G01N 27/125
USPC ......................................... 73/31.06
See application file for complete search history.

(56) References Cited

U.S. PATENT DOCUMENTS

| | | | |
|---|---|---|---|
| 2017/0131227 A1 | 5/2017 | Homma et al. | |
| 2017/0269043 A1* | 9/2017 | Homma | G01N 33/005 |
| 2019/0353606 A1* | 11/2019 | Wei | B60L 58/30 |
| 2020/0083549 A1* | 3/2020 | Kawai | B60L 3/0053 |
| 2022/0003706 A1* | 1/2022 | Suzuki | G01N 27/128 |

FOREIGN PATENT DOCUMENTS

| | | |
|---|---|---|
| JP | 2017-022938 A | 1/2017 |
| WO | 2017/037984 A1 | 3/2017 |

OTHER PUBLICATIONS

International Search Report issued on May 25, 2021 in International Patent Application No. PCT/JP2021/014645, with English translation.

* cited by examiner

*Primary Examiner* — Nathaniel T Woodward
(74) *Attorney, Agent, or Firm* — Rimon P.C.

(57) ABSTRACT

A hydrogen sensor includes: a first electrode which is planar; a second electrode which is planar, faces the first electrode, and includes an exposed portion; a metal oxide layer which is sandwiched between a surface of the first electrode and a surface of the second electrode, and has a resistance that changes due to hydrogen; and two terminals, i.e., a first terminal and a second terminal, that are connected to the second electrode.

13 Claims, 13 Drawing Sheets

HYDROGEN SENSOR, HYDROGEN DETECTION METHOD, AND HYDROGEN DETECTION DEVICE

CROSS REFERENCE TO RELATED APPLICATIONS

This is a continuation application of PCT International Application No. PCT/JP2021/014645 filed on Apr. 6, 2021, designating the United States of America, which is based on and claims priority of Japanese Patent Application No. 2020-073461 filed on Apr. 16, 2020. The entire disclosures of the above-identified applications, including the specifications, drawings and claims are incorporated herein by reference in their entirety.

FIELD

The present disclosure relates to a hydrogen sensor, a hydrogen detection method, and a hydrogen detection device.

BACKGROUND

Patent Literature (PTL) 1 and PTL 2 disclose a gas sensor that detects gas molecules containing hydrogen atoms.

CITATION LIST

Patent Literature

[PTL 1] International Publication WO2017/037984
[PTL 2] Japanese Unexamined Patent Application Publication No. 2017-22938

SUMMARY

Technical Problem

The conventional techniques, however, have a problem of low performance in detecting low-concentrated hydrogen in particular.

In view of the above, the present disclosure provides a hydrogen sensor, a hydrogen detection method, and a hydrogen detection device whose performance in detecting low-concentrated hydrogen is improved.

Solution to Problem

A hydrogen sensor according to an aspect of the present disclosure includes: a first electrode which is planar; a second electrode which is planar, faces the first electrode, and includes an exposed portion; a metal oxide layer which is sandwiched between a surface of the first electrode and a surface of the second electrode facing each other, and has a resistance that changes due to hydrogen; and two terminals connected to the second electrode.

A hydrogen detection method according to an aspect of the present disclosure is a hydrogen detection method in a hydrogen sensor, the hydrogen sensor including: a first electrode which is planar; a second electrode which is planar, faces the first electrode, and includes an exposed portion; a metal oxide layer which is sandwiched between a surface of the first electrode and a surface of the second electrode facing each other, and has a resistance that changes due to hydrogen; and two terminals connected to the second electrode with the exposed portion being interposed therebetween in plan view of the second electrode, the hydrogen detection method including: passing a current through the exposed portion by applying a voltage between the two terminals; and detecting a gas containing hydrogen atoms by detecting a decrease in a resistance value between the first electrode and the second electrode or by detecting a decrease in a resistance value between the two terminals.

A hydrogen detection device according to an aspect of the present disclosure includes: a first electrode which is planar; a second electrode which is planar, faces the first electrode, and includes an exposed portion; a metal oxide layer which is sandwiched between a surface of the first electrode and a surface of the second electrode facing each other, and has a resistance that changes due to hydrogen; two terminals connected to the second electrode; and a drive circuit that, in a state of passing a current through the exposed portion by applying a voltage between the two terminals, detects a gas containing hydrogen atoms by detecting a decrease in a resistance value between the first electrode and the second electrode or by detecting a decrease in a resistance value between the two terminals.

Advantageous Effects

A hydrogen sensor, a hydrogen detection method, and a hydrogen detection device according to the present disclosure can improve the performance in detecting low-concentrated hydrogen.

BRIEF DESCRIPTION OF DRAWINGS

These and other advantages and features will become apparent from the following description thereof taken in conjunction with the accompanying Drawings, by way of non-limiting examples of embodiments disclosed herein.

DESCRIPTION OF EMBODIMENTS

Hereinafter, embodiments are specifically described with reference to the drawings.

Note that each of the embodiments described below shows a general or specific example. The numerical values, shapes, materials, constituent elements, the arrangement and connection of the constituent elements, steps, the processing order of the steps etc. illustrated in the embodiments described below are mere examples, and are not intended to limit the present disclosure.

Embodiment 1

[1.1 Configuration of Hydrogen Sensor 1]

Figure 1A:
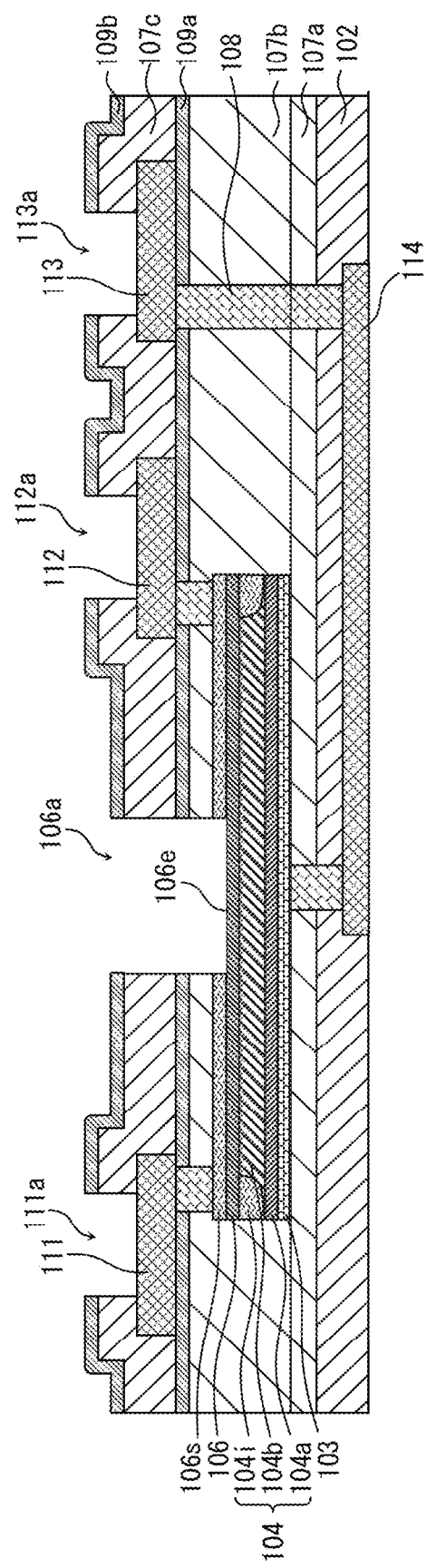
FIG. 1A is a cross-sectional view illustrating a configuration example of a hydrogen sensor according to Embodiment 1.
Figure 1B:
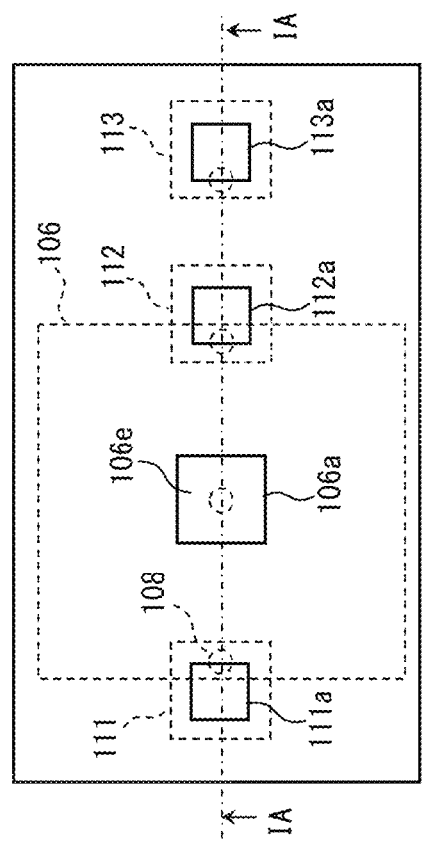
FIG. 1B is a top view illustrating a configuration example of the hydrogen sensor according to Embodiment 1.

FIG. 1A is a cross-sectional view illustrating a configuration example of hydrogen sensor 1 according to Embodiment 1. FIG. 1B is a top view illustrating a configuration example of hydrogen sensor 1 according to Embodiment 1. Note that FIG. 1A illustrates a schematic cross section along line IA-IA of FIG. 1B, viewed in the arrow direction.

As illustrated in FIG. 1A and FIG. 1B, key components of hydrogen sensor 1 include first electrode 103, metal oxide layer 104, second electrode 106, first terminal 111, second terminal 112, and third terminal 113. The key components of hydrogen sensor 1 are covered by insulating film 102, insulating films 107a through 107c, and insulating films 109a and 109b. These insulating films, however, have openings 106a, 111a, 112a, and 113a.

First electrode 103 is a planar electrode and has two surfaces. Of the two surfaces of first electrode 103, one surface (i.e., the upper surface in FIG. 1A) is in contact with metal oxide layer 104, and the other surface (i.e., the lower surface in FIG. 1A) is in contact with insulating film 107b and via 108. In FIG. 1B, first electrode 103 is in a rectangular shape of the same size as that of second electrode 106. First electrode 103 may include, for example, a material having a standard electrode potential lower than that of metals forming metal oxides, such as tungsten, nickel, tantalum, titanium, aluminum, tantalum nitride, and titanium nitride. The higher the value of the standard electrode potential is, the more resistant to oxidation the material is. First electrode 103 in FIG. 1A is formed with, for example, tantalum nitride (TaN) or titanium nitride (TiN), or laminations thereof.

Metal oxide layer 104 is sandwiched between a surface of first electrode 103 and a surface of second electrode 106 facing each other, is formed with a metal oxide serving as a gas-sensitive resistance film, and has a resistance value that reversibly changes according to the presence and absence of a hydrogen-containing gas in a gas in contact with second electrode 106. It is sufficient so long as metal oxide layer 104 has a property that its resistance is changed by hydrogen. Metal oxide layer 104 is formed with an oxygen-deficient metal oxide. As the base metal of metal oxide layer 104, at least one of the following may be selected: aluminum (Al) and transition metals such as tantalum (Ta), hafnium (Hf), titanium (Ti), zirconium (Zr), niobium (Nb), tungsten (W), nickel (Ni), and iron (Fe). Since transition metals can take on plural oxidation states, different resistance states can be realized through redox reactions. Here, the "degree of oxygen deficiency" of a metal oxide is the ratio of deficiency of oxygen in the metal oxide to the amount of oxygen in an oxide having a stoichiometric composition composed of the same elements as those of the metal oxide. Here, the oxygen deficiency is a value obtained by subtracting the amount of oxygen in the metal oxide from the amount of oxygen in the metal oxide having a stoichiometric composition. If there can be two or more metal oxides having stoichiometric compositions composed of the same elements as those of the metal oxide, the degree of oxygen deficiency of the metal oxide is defined based on one of the two or more metal oxides having stoichiometric compositions that has the highest resistance value. Metal oxides having stoichiometric compositions are more stable and higher in resistance value than metal oxides having other compositions. For example, when the base metal of metal oxide layer 104 is tantalum (Ta), the oxide having a stoichiometric composition as defined above is $Ta_2O_5$, so metal oxide layer 104 can be expressed as $TaO_{2.5}$. The degree of oxygen deficiency of $TaO_{2.5}$ is 0%, and the degree of oxygen deficiency of $TaO_{1.5}$ is $(2.5-1.5)/2.5=40\%$. The degree of oxygen deficiency of a metal oxide with excess oxygen is a negative value. Note that in the present disclosure, the degree of oxygen deficiency can take a positive value, 0, or a negative value unless otherwise noted. An oxide with a low degree of oxygen deficiency has a high resistance value because it is closer to an oxide having a stoichiometric composition, whereas an oxide with a high degree of oxygen deficiency has a low resistance value because it is closer to the metal included in the oxide.

Metal oxide layer 104 illustrated in FIG. 1A includes: first layer 104a in contact with first electrode 103; second layer 104b in contact with first layer 104a and second electrode 106; and isolation layer 104i. The degree of oxygen deficiency of second layer 104b is lower than that of first layer 104a. For example, first layer 104a is TaOx. Second layer 104b is $Ta_2O_5$ whose degree of oxygen deficiency is lower than that of first layer 104a. Metal oxide layer 104 includes isolation layer 104i at the perimeter in plan view of first electrode 103.

Here, plan view means viewing hydrogen sensor 1 according to the present disclosure from a viewpoint in the layer-stacking direction in FIG. 1A; in other words, viewing from a viewpoint in the direction normal to any of the surfaces of, for example, first electrode 103 and second electrode 106 that are planar. For example, plan view refers to viewing the top surface of hydrogen sensor 1 illustrated in FIG. 1B.

The resistance state of such metal oxide layer 104 is that the resistance value decreases according to a hydrogen-containing gas that comes into contact with second electrode 106. In detail, when a hydrogen-containing gas is present in a detection-target gas, hydrogen atoms are dissociated from the hydrogen-containing gas in second electrode 106. The dissociated hydrogen atoms enter metal oxide layer 104 and form impurity levels. In particular, the dissociated hydrogen atoms concentrate in the vicinity of the interface with the second electrode, making the apparent thickness of second layer 104b smaller. As a result, the resistance value of metal oxide layer 104 decreases.

Second electrode 106 is a planar electrode with hydrogen dissociability, and has two surfaces. Of the two surfaces of second electrode 106, one surface (i.e., the lower surface in FIG. 1A) is in contact with metal oxide layer 104, and the other surface (i.e., the upper surface in FIG. 1A) is in contact with metal layer 106s and the outside air. Second electrode 106 has, in aperture 106a, exposed portion 106e that is exposed to the outside air. Second electrode 106 is formed with, for example, a material that catalyzes dissociation of hydrogen atoms from gas molecules having hydrogen atoms, such as platinum (Pt), iridium (Ir), palladium (Pd), or nickel (Ni), or an alloy containing at least one of these. It is assumed that second electrode 106 in FIG. 1A is platinum (Pt). Two terminals, namely first terminal 111 and second terminal 112, are connected to second electrode 106.

First terminal 111 is connected to second electrode 106 through via 108.

Second terminal 112 is connected to second electrode 106 through via 108. First terminal 111 and second terminal 112 are connected, via openings 111a and 112a, respectively, to an external drive circuit that drives hydrogen sensor 1.

As illustrated in FIG. 1B, first terminal 111 and second terminal 112 are disposed with exposed portion 106e being interposed therebetween in plan view of second electrode 106. With first terminal 111 and second terminal 112 disposed in this manner, application of a predetermined voltage between first terminal 111 and second terminal 112 causes passage of current through exposed portion 106e of second electrode 106, that is, causes current to flow through exposed portion 106e. The passage of current through exposed portion 106e of second electrode 106 is considered to activate the hydrogen dissociation by exposed portion 106e. Note that the predetermined voltage may be voltages that are opposite to each other in polarity.

In hydrogen sensor 1, the resistance value between first terminal 111 and second terminal 112 changes when gas molecules containing hydrogen atoms come into contact with exposed portion 106e during the passage of a current through exposed portion 106e. By the above-described drive circuit detecting this change in the resistance value, gas molecules containing hydrogen atoms are detected.

Third terminal 113 is connected to first electrode 103 via opening 113a, via 108, wiring 114, and via 108. Third terminal 113 is connected, via opening 113a, to the external drive circuit that drives hydrogen sensor 1. In hydrogen sensor 1, the resistance between first electrode 103 and second electrode 106 changes when gas molecules containing hydrogen atoms come into contact with exposed portion 106e during the passage of a current through exposed portion 106e. In other words, in hydrogen sensor 1, the resistance value between first terminal 111 or second terminal 112 and third terminal 113 changes when gas molecules containing hydrogen atoms come into contact with exposed portion 106e during the passage of a current through exposed portion 106e. Gas molecules containing hydrogen atoms are detected also through detection, by the above-described drive circuit, of the change in the resistance value.

Note that insulating film 102, insulating films 107a through 107c, and insulating films 109a and 109b that cover the key components of hydrogen sensor 1 are formed with a silicon oxide film, a silicon nitride film, etc.

Metal layer 106s is formed on the upper surface of second electrode 106 except for opening 106a. Metal layer 106s includes, for example, TiAlN as the material, and is formed as an etching stopper for forming vias 108, but is not essential.

The laminate of first electrode 103, metal oxide layer 104, and second electrode 106 is a structure that can be used as a storage element of resistance random access memory (ReRAM). The storage element of the resistance random access memory is a digital storage element which uses two of possible states that metal oxide layer 104 can take, i.e., a high-resistance state and a low-resistance state. Hydrogen sensor 1 according to the present disclosure uses the high-resistance state among the possible states of metal oxide layer 104.

FIG. 1A illustrates an example of metal oxide layer 104 having a two-layer configuration with first layer 104a that includes TaOx as the material and second layer 104b that includes, as the material, $Ta_2O_5$ whose degree of oxygen deficiency is low. However, metal oxide layer 104 may have a one-layer configuration having, as the material, TaOx or $Ta_2O_5$ whose degree of oxygen deficiency is low.

[1.2 Hydrogen Detection Method and Hydrogen Detection Device]

Next, a hydrogen detection method performed using hydrogen sensor 1 and a hydrogen detection device including hydrogen sensor 1 are described.

Figure 2:
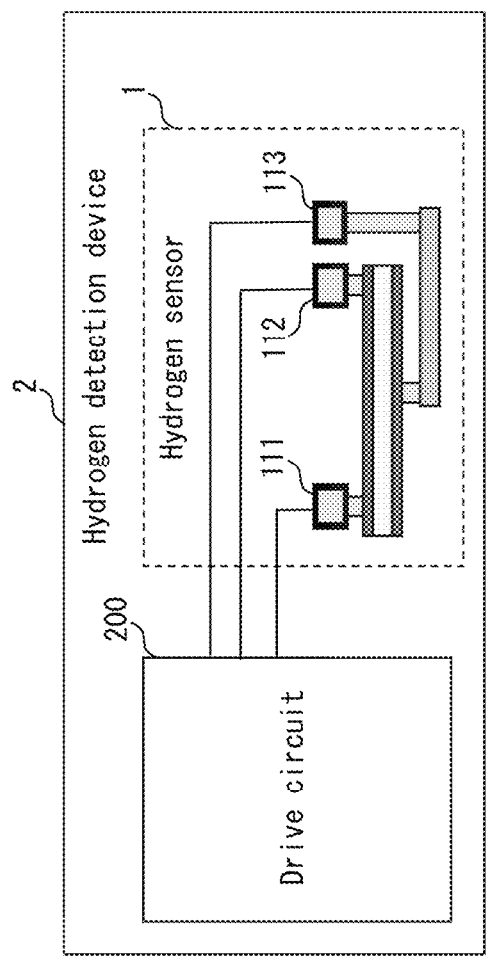
FIG. 2 is a block diagram illustrating a configuration example of a hydrogen detection device including a hydrogen sensor and a drive circuit that performs a hydrogen detection method according to Embodiment 1.

FIG. 2 is a block diagram illustrating a configuration example of hydrogen detection device 2 including hydrogen sensor 1 and drive circuit 200 that performs a hydrogen detection method according to Embodiment 1. In FIG. 2, hydrogen detection device 2 includes drive circuit 200 and hydrogen sensor 1. Drive circuit 200 is connected to hydrogen sensor 1 via at least three wires connected to first terminal 111, second terminal 112, and third terminal 113 of hydrogen sensor 1. Drive circuit 200 is a microcomputer including, for example, a central processing unit (CPU), read-only memory (ROM), and random-access memory (RAM). At least three wires are connected to ports of the microcomputer.

Figure 3:
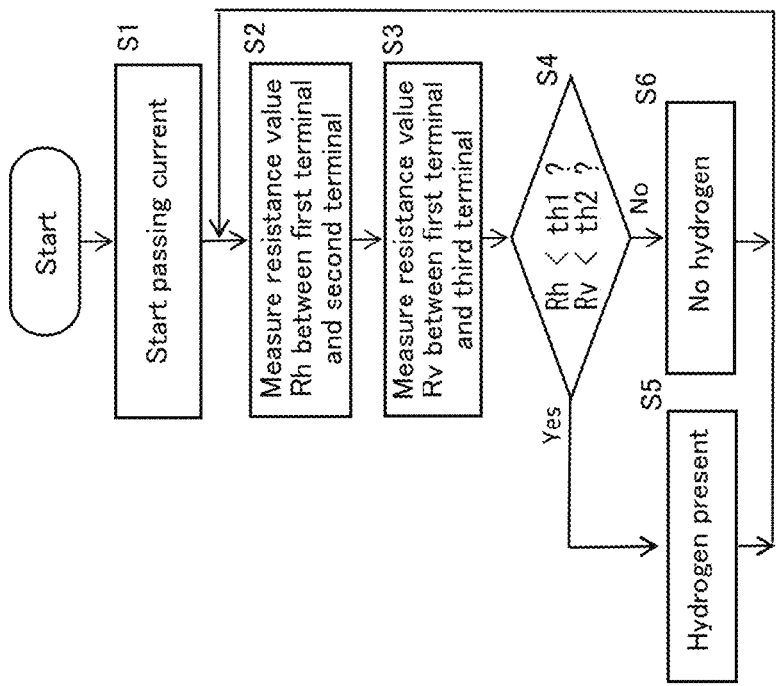
FIG. 3 is a flowchart illustrating a hydrogen detection method performed by the drive circuit using the hydrogen sensor according to Embodiment 1.

FIG. 3 is a flowchart illustrating a hydrogen detection method performed by drive circuit 200 using hydrogen sensor 1. In FIG. 3, drive circuit 200 first starts passing current between first terminal 111 and second terminal 112 (S1). In other words, drive circuit 200 applies a predetermined voltage between first terminal 111 and second terminal 112. For example, voltages that are opposite to each other in polarity, e.g., +V1 and −V1, are applied to first terminal 111 and second terminal 112. The current that passes through exposed portion 106e of second electrode 106 as a result of the voltage application is sufficient so long as it is in a range from several milliamperes to several tens of milliamperes, for example.

Next, drive circuit 200 measures resistance value Rh between first terminal 111 and second terminal 112 (S2), and further measures resistance value Rv between first terminal 111 or second terminal 112 and third terminal 113 (S3). Furthermore, drive circuit 200 determines whether measured resistance value Rh is less than threshold th1, and determines whether measured resistance value Rv is less than threshold th2 (S4). If at least one of resistance values Rh and Rv is determined to be less than the threshold, it is determined as "hydrogen present" (S5), and if not, it is determined as "no hydrogen" (S6).

Drive circuit 200 may repeat steps S2 through S6 at a constant cycle of several hundreds of milliseconds to several seconds, for example.

Note that FIG. 3 illustrates an example of constantly passing a current between first terminal 111 and second terminal 112; however, a current may be passed only during the processing of steps S2 and S3.

In step S5, it may be determined as "hydrogen present" if resistance value Rh and resistance value Rv are both determined to be less than the respective thresholds.

One of steps S2 and S3 may be omitted, and only one of resistance values Rh and Rv may be used for the determination.

[1.3 Experimental Data]

Next, operations of hydrogen sensor 1 according to Embodiment 1 are described using experimental data.

Figure 4:
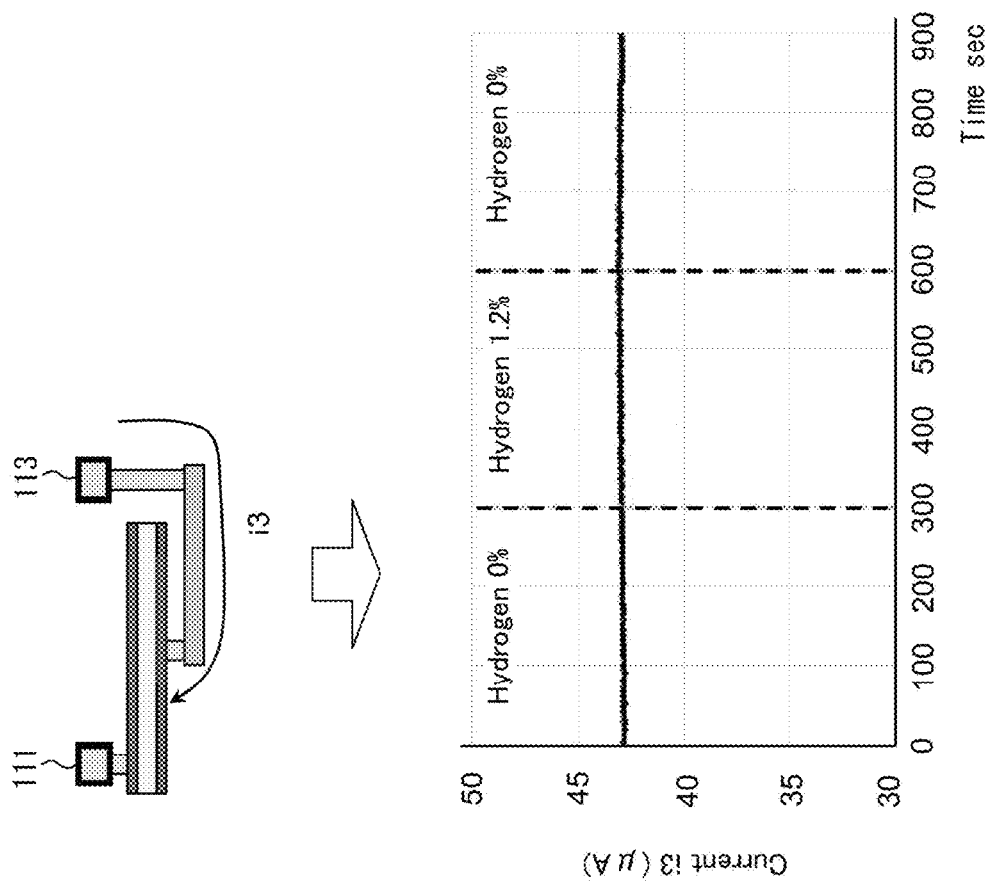
FIG. 4 illustrates an experimental result of a hydrogen sensor of a comparative example.

FIG. 4 illustrates experimental data on a hydrogen sensor of a comparative example. Compared to hydrogen sensor 1 according to Embodiment 1, the hydrogen sensor of the comparative example has a configuration which does not include second terminal 112 or the same configuration as hydrogen sensor 1 of Embodiment 1 except that first terminal 111 and second terminal 112 are short-circuited. In FIG. 4, the horizontal axis represents time. The vertical axis represents current i3 between third terminal 113 and first terminal 111, that is, current i3 flowing between first electrode 103 and second electrode 106. The measurement conditions are as follows: a voltage of typically 1.2 V is applied between third terminal 113 and first terminal 111, and a voltage of −2.2 V is applied therebetween for 50 milliseconds for every second. Also, during the time period from 0 to 300 in seconds, exposed portion 106e of second electrode 106 is in contact with a gas containing 0% of hydrogen. During the time period from 300 to 600 in seconds, exposed portion 106e of second electrode 106 is in contact with a gas containing 1.2% of hydrogen. During the time period from 600 to 900 in seconds, exposed portion 106e of second electrode 106 is in contact with a gas containing 0% of hydrogen.

With the hydrogen sensor of the comparative example under these measurement conditions, current i3 was constant regardless of the presence or absence of hydrogen as illustrated in FIG. 4. In other words, the hydrogen sensor of the comparative example did not react to the gas containing 1.2% of hydrogen and could not detect hydrogen.

Figure 5:
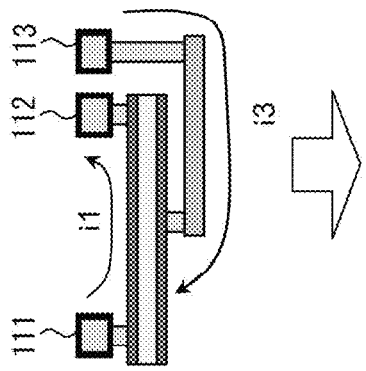
FIG. 5 illustrates an experimental result of the hydrogen sensor according to Embodiment 1.
Figure 5:
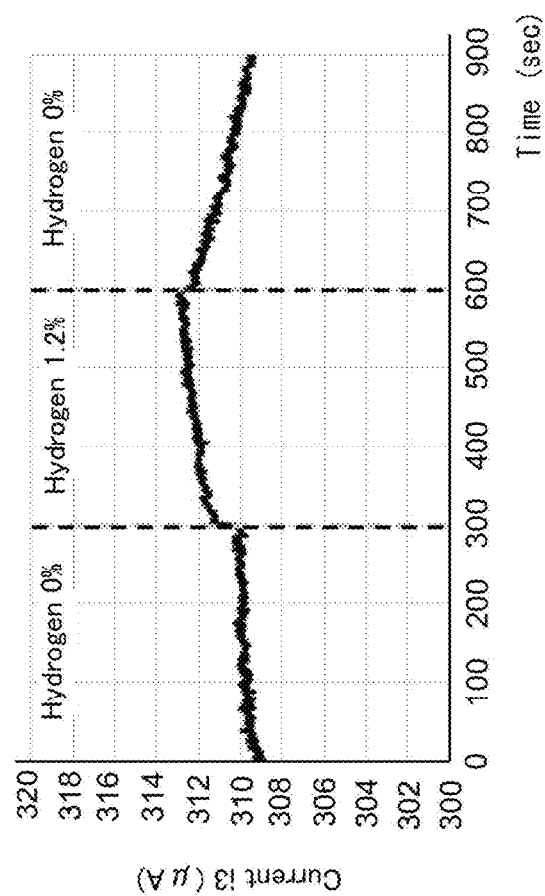

FIG. 5 illustrates an experimental result of hydrogen sensor 1 according to Embodiment 1. The horizontal axis of FIG. 5 represents the same time axis as in FIG. 4. The vertical axis represents current i3 between third terminal 113 and first terminal 111, that is, current i3 flowing between first electrode 103 and second electrode 106. The measurement conditions are different from those in FIG. 4 in that a condition of passing a current between first terminal 111 and second terminal 112 is added. In other words, in FIG. 5, a current of about 11 mA is applied between first terminal 111 and second terminal 112.

With hydrogen sensor 1 according to Embodiment 1 under these measurement conditions, current i3 increases in the time period from 300 to 600 in seconds as compared to the other time periods. In other words, in the time period from 300 to 600 in seconds, hydrogen atoms are dissociated from the gas that has come into contact with exposed portion 106e of second electrode 106, and the dissociated hydrogen atoms enter metal oxide layer 104 and form impurity levels, causing a decrease in the resistance value of metal oxide layer 104. As a result, current i3 increases in the time period from 300 to 600 in seconds. Furthermore, in the time period from 600 to 900 in seconds, current i3 decreases as compared to the previous time period. According to FIG. 5, the current between first terminal 111 and third terminal 113 increases and decreases in response to the presence and absence of hydrogen. It can be understood that the hydrogen detection performance of hydrogen sensor 1 is improved as compared to that of the hydrogen sensor illustrated in FIG. 4.

Figure 6:
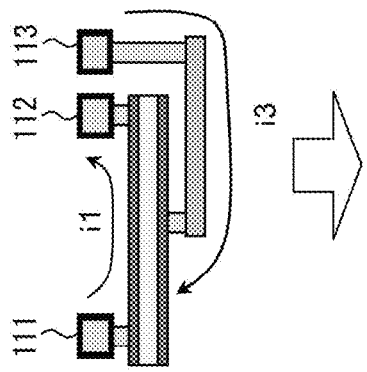
FIG. 6 illustrates an experimental result of the hydrogen sensor according to Embodiment 1.
Figure 6:
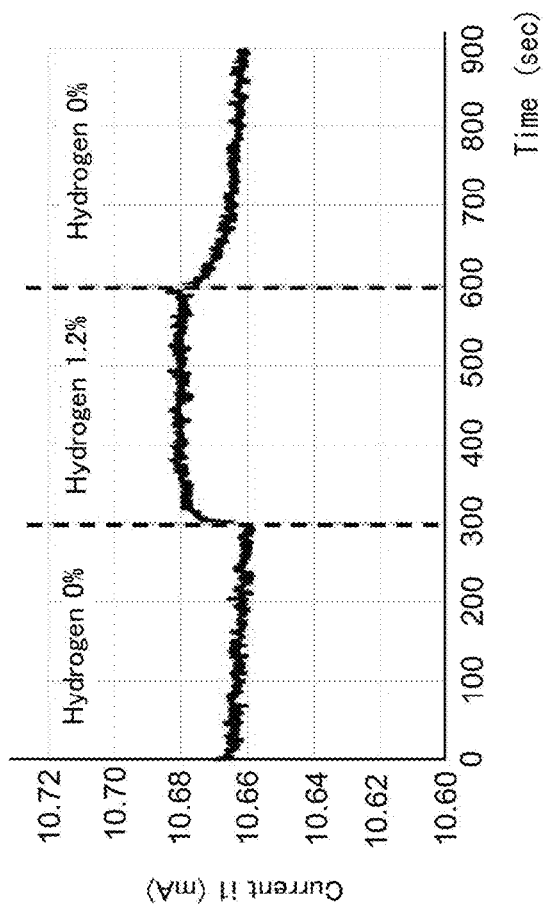

FIG. 6 illustrates an experimental result of hydrogen sensor 1 according to Embodiment 1. The horizontal axis of FIG. 6 represents the same time axis as in FIG. 4. The vertical axis of FIG. 6 is different from that of FIG. 5, and represents current i1 between first terminal 111 and second terminal 112. The measurement conditions are the same as those in FIG. 5. However, it is assumed that, for example, voltages that are opposite to each other in polarity, such as +0.1 V and −0.1 V, are applied to first terminal 111 and second terminal 112 and a current of about 11 mA is passed through first terminal 111 and second terminal 112. Note that the value of the current passed is determined based on the resistance value of second electrode 106.

With hydrogen sensor 1 according to Embodiment 1 under these measurement conditions, current i1 increases in the time period from 300 to 600 in seconds as compared to the other time periods. Furthermore, in the time period from 600 to 900 in seconds, current i1 decreases as compared to the previous time period. According to FIG. 6, the current between first terminal 111 and second terminal 112 increases and decreases in response to the presence and absence of hydrogen.

Comparison between FIG. 4 and FIGS. 5 and 6 shows that the passage of a current between first terminal 111 and second terminal 112 leads to an improvement in the hydrogen detection capability. Moreover, as a result of exposed portion 106e coming into contact with hydrogen, the resistance between first terminal 111 and third terminal 113 decreases, and the resistance between first terminal 111 and second terminal 112 also decreases. In other words, hydrogen detection is possible in two ways. That is to say, one way of hydrogen detection is through a change in the resistance between first terminal 111 and second terminal 112, and another way of hydrogen detection is through a change in the resistance between first terminal 111 and third terminal 113.

As described above, hydrogen sensor 1 according to Embodiment 1 includes: first electrode 103 which is planar; second electrode 106 which is planar, faces first electrode 103, and includes exposed portion 106e; metal oxide layer 104 which is sandwiched between a surface of first electrode 103 and a surface of second electrode 106 facing each other, and has a resistance that changes due to hydrogen; and first terminal 111 and second terminal 112 as two terminals connected to second electrode 106.

With this, since hydrogen sensor 1 includes two terminals for passing a current through second electrode 106, passage of a current can lead to an improvement in the hydrogen detection performance.

Here, the two terminals, i.e., first terminal 111 and second terminal 112, may be positioned with exposed portion 106e being interposed therebetween in plan view of second electrode 106 which is planar.

With this, it is possible to pass a current through exposed portion 106e that comes into contact with a gas, and the hydrogen detection performance can be efficiently improved.

Here, a current may be passed through exposed portion 106e by applying predetermined voltages to two terminals 111 and 112.

Here, voltages opposite to each other in polarity may be applied to the two terminals as predetermined voltages.

With this, the voltage applied to the central part of exposed portion 106e can be made substantially 0 V, and the hydrogen detection performance can be efficiently improved.

Here, in hydrogen sensor 1, a resistance between first electrode 103 and second electrode 106 may change when gas molecules containing hydrogen atoms come into contact with exposed portion 106e during passage of a current through exposed portion 106e.

With this, hydrogen can be detected through a change in the resistance between first electrode 103 and second electrode 106.

Here, in hydrogen sensor 1, a resistance between the two terminals may change when gas molecules containing hydrogen atoms come into contact with exposed portion 106e during passage of a current through exposed portion 106e.

With this, hydrogen can be detected through a change in the resistance between the two terminals, i.e., first terminal 111 and second terminal 112.

Here, hydrogen sensor 1 may include: a first via which is connected to, of two main surfaces of first electrode 103, a main surface farther from metal oxide layer 104, and overlaps with exposed portion 106e in plan view of second electrode 106 which is planar; and a connection terminal (i.e., third terminal 113) connected to the first via.

Here, the two terminals may be connected to second electrode 106 via two second vias connected to second electrode 106, and the first via may be located at a central position between the two second vias.

With this configuration, first terminal 111 and second terminal 112 are disposed approximately symmetrically about exposed portion 106e through which a current is passed, and thus, a key current path between first electrode 103 and second electrode 106 can be formed at the central part of exposed portion 106e. As a result, the hydrogen detection performance can be improved.

Here, metal oxide layer 104 may include (i) first layer 104a in contact with first electrode 103 and (ii) second layer 104b in contact with first layer 104a and second electrode 106, and second layer 104b may have a degree of oxygen deficiency lower than a degree of oxygen deficiency of first layer 104a.

With this, the gas sensitivity of second layer 104b for the hydrogen atoms dissociated by second electrode 106 can be enhanced.

A hydrogen detection method according to Embodiment 1 is a hydrogen detection method in a hydrogen sensor, the hydrogen sensor including: first electrode 103 which is planar; second electrode 106 which is planar, faces first electrode 103, and includes exposed portion 106e; metal oxide layer 104 which is sandwiched between a surface of first electrode 103 and a surface of second electrode 106 facing each other, and has a resistance that changes due to hydrogen; and two terminals (i.e., first terminal 111 and second terminal 112) connected to second electrode 106 with exposed portion 106e being interposed therebetween in plan view of second electrode 106 which is planar, the hydrogen detection method including: passing a current through exposed portion 106e by applying a voltage between the two terminals; and detecting a gas containing hydrogen atoms by detecting a decrease in a resistance value between first electrode 103 and second electrode 106 or by detecting a decrease in a resistance value between first terminal 111 and second terminal 112.

With this, passage of a current between the two terminals, i.e., first terminal 111 and second terminal 112, can lead to an improvement in the hydrogen detection performance.

Hydrogen detection device 2 according to Embodiment 1 includes: first electrode 103 which is planar; second electrode 106 which is planar, faces first electrode 103, and includes exposed portion 106e; metal oxide layer 104 which is sandwiched between a surface of first electrode 103 and a surface of second electrode 106, and has a resistance that changes due to hydrogen; two terminals (i.e., first terminal 111 and second terminal 112) connected to second electrode 106; and drive circuit 200 that, in a state of passing a current through exposed portion 106e by applying a voltage between the two terminals, detects a gas containing hydrogen atoms by detecting a decrease in a resistance value between first electrode 103 and second electrode 106 or by detecting a decrease in a resistance value between the two terminals.

With this, passage of a current between the two terminals, i.e., first terminal 111 and second terminal 112, can lead to an improvement in the hydrogen detection performance.

Embodiment 2

In Embodiment 2, a configuration example of hydrogen sensor 1 is described. Hydrogen sensor 1 according to Embodiment 2 includes, in addition to the elements of hydrogen sensor 1 according to Embodiment 1, a local region called a filament inside metal oxide layer 104. With hydrogen sensor 1 that includes the local region, the hydrogen detection performance can be further enhanced and the reaction speed in the hydrogen detection can be further increased.

[2.1 Configuration of Hydrogen Sensor 1]

Figure 7:
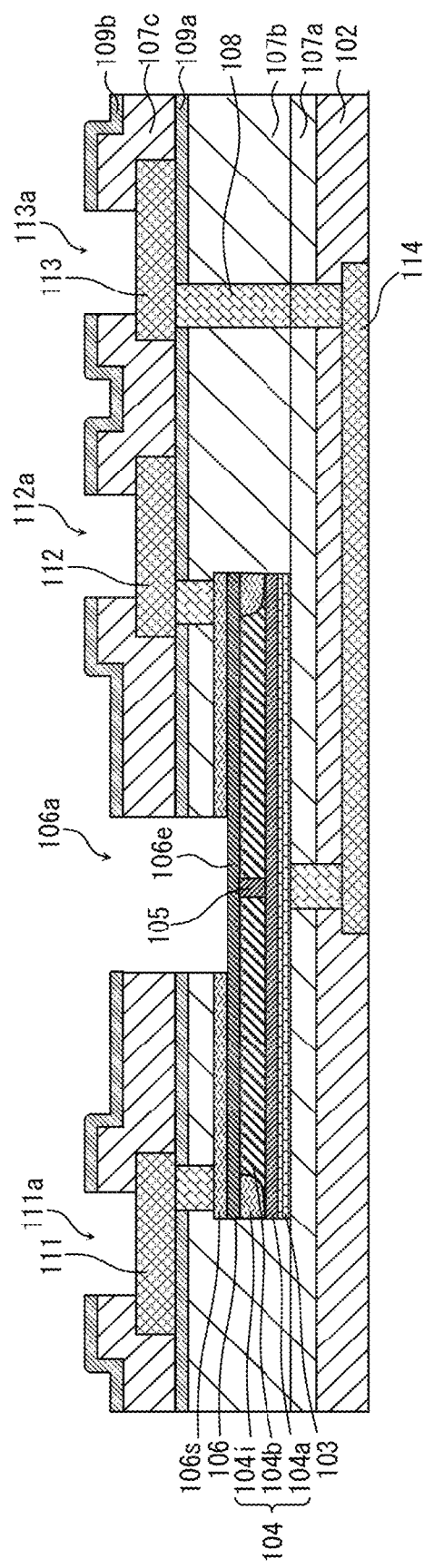
FIG. 7 is a cross-sectional view illustrating a configuration example of a hydrogen sensor according to Embodiment 2.

FIG. 7 is a cross-sectional view illustrating a configuration example of hydrogen sensor 1 according to Embodiment 2. Hydrogen sensor 1 in FIG. 7 is different from hydrogen sensor 1 in FIG. 1A in that local region 105 is added. Hereinafter, different aspects are mainly described, and overlapping descriptions of the same aspects are avoided.

Local region 105 is a region which is not in contact with first electrode 103 but is in contact with second electrode 106, and whose degree of oxygen deficiency is higher than that of metal oxide layer 104 surrounding local region 105. Local region 105 is a region in which current flows more easily than in metal oxide layer 104. That is to say, local region 105 is a minute region that includes a filament (a conductive path) formed by oxygen vacancies. In addition, local region 105 is formed at approximately the central part of exposed portion 106e in plan view of second electrode 106. Local region 105 or the filament is formed by a process called forming. In the forming process, a pulse that serves as an electrical stress is applied between second electrode 106 and first electrode 103. Local region 105 can be formed with dependence on the magnitude and duration of the pulse.

FIG. 7 illustrates an example of metal oxide layer 104 having a two-layer configuration with first layer 104a that includes TaOx as the material and second layer 104b that includes, as the material, $Ta_2O_5$ whose degree of oxygen deficiency is low. However, metal oxide layer 104 may have a one-layer configuration having, as the material, TaOx or $Ta_2O_5$ whose degree of oxygen deficiency is low.

[2.2 Experimental Data]

Next, operations of hydrogen sensor 1 according to Embodiment 2 are described using experimental data.

Figure 8:
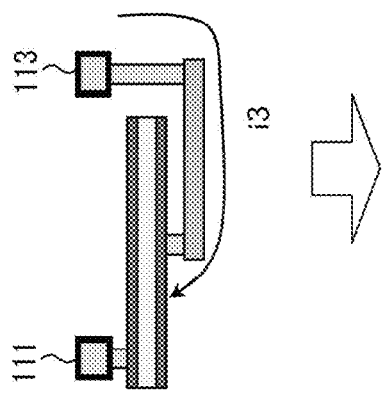
FIG. 8 illustrates an experimental result of a hydrogen sensor of a comparative example.
Figure 8:
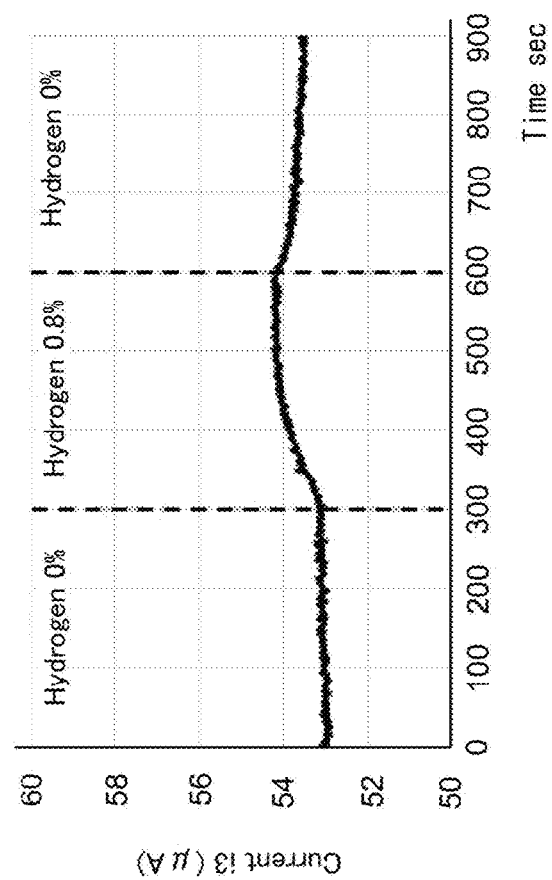

FIG. 8 illustrates experimental data on a hydrogen sensor of a comparative example. Compared to hydrogen sensor 1 according to Embodiment 2, the hydrogen sensor of the comparative example has a configuration which does not include second terminal 112 or the same configuration as hydrogen sensor 1 of Embodiment 2 except that first terminal 111 and second terminal 112 are short-circuited. The measurement conditions in FIG. 8 are the same as those in FIG. 4.

Under the same measurement conditions as in FIG. 4, the hydrogen sensor of the comparative example reacted to hydrogen but the increase over time of current i3 was gradual, as illustrated in FIG. 8.

Figure 9:
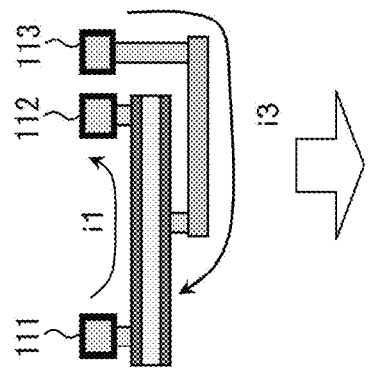
FIG. 9 illustrates an experimental result of the hydrogen sensor according to Embodiment 2.
Figure 9:
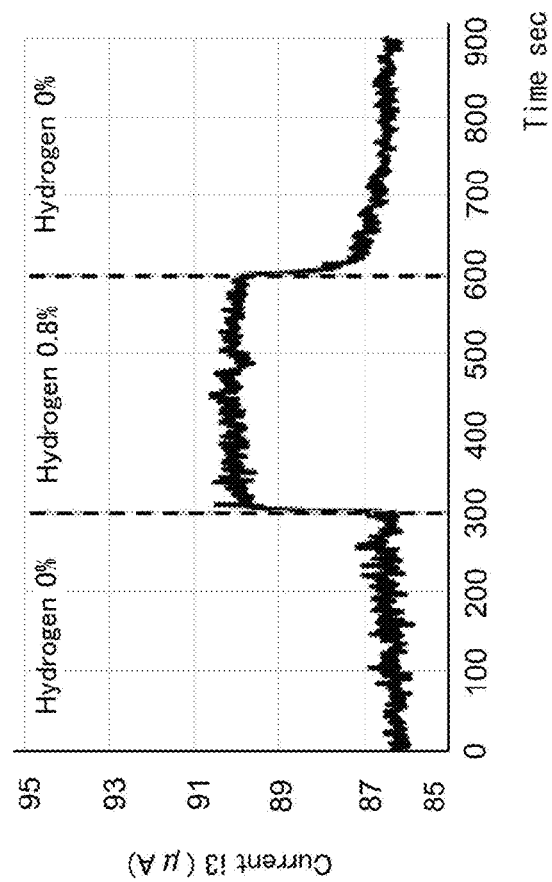

FIG. 9 illustrates an experimental result of hydrogen sensor 1 according to Embodiment 2. The measurement conditions in FIG. 9 are the same as those in FIG. 5.

In hydrogen sensor 1 according to Embodiment 2, current i3 increased in the time period from 300 to 600 in seconds as compared to the other time periods, and the increase over time of current i3 was rapid as illustrated in FIG. 9. In other words, in the time period from 300 to 600 in seconds, hydrogen atoms are dissociated more quickly from the gas that has come into contact with exposed portion 106e of second electrode 106, and the dissociated hydrogen atoms enter metal oxide layer 104 and form impurity levels, causing a decrease in the resistance value of metal oxide layer 104. As a result, current i3 rapidly increases in the time period from 300 to 600 in seconds. Furthermore, in the time period from 600 to 900 in seconds, current i3 decreases as compared to the previous time period. According to FIG. 9, the current between first terminal 111 and third terminal 113 increases and decreases in response to the presence and absence of hydrogen. The amount of change in FIG. 9 is greater than that in FIG. 5.

As described above, hydrogen sensor 1 according to Embodiment 2 includes a local region which is located inside metal oxide layer 104, is in contact with second electrode 106, and has a degree of oxygen deficiency higher than a degree of oxygen deficiency of metal oxide layer 104.

With this, the hydrogen detection performance can be improved, and the response speed in the hydrogen detection can be increased.

Hydrogen sensor 1 includes a local region which is located inside metal oxide layer 104, is in contact with second electrode 106, and is a region in which current flows more easily than in metal oxide layer 104.

With this, too, the hydrogen detection performance can be improved, and the response speed in the hydrogen detection can be increased.

Embodiment 3

In Embodiment 3, a configuration example of hydrogen sensor 1 is described. Hydrogen sensor 1 according to Embodiment 3 is different from hydrogen sensor 1 according to Embodiment 1 In that metal oxide layer 104 has a three-layer configuration. With this configuration example, the hydrogen detection performance can be further enhanced, and the response speed in the hydrogen detection can be further increased.

[3.1 Configuration of Hydrogen Sensor 1]

Figure 10:
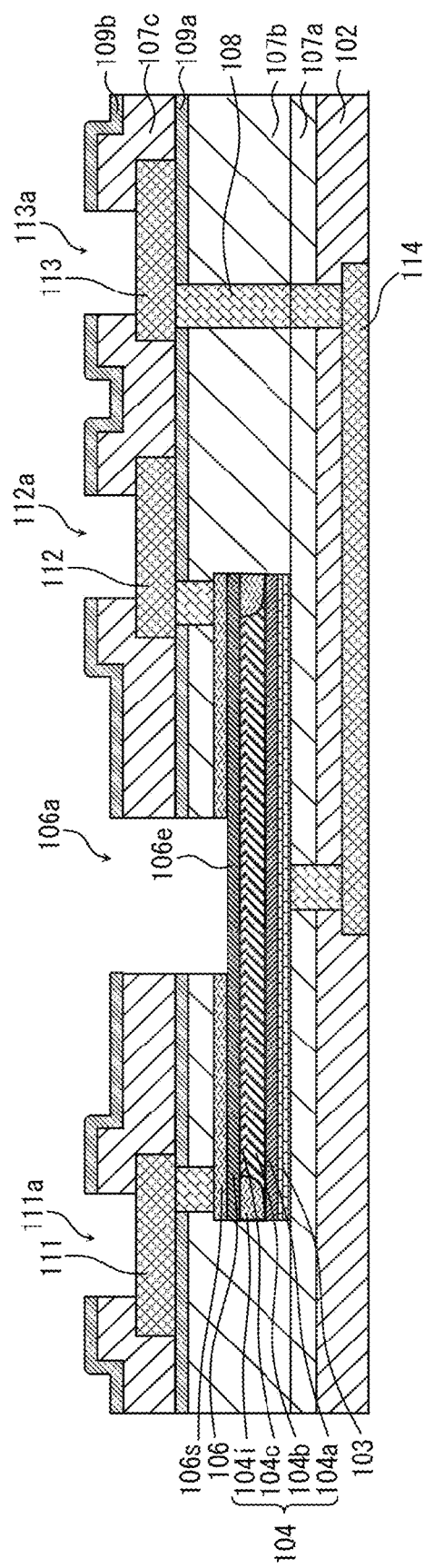
FIG. 10 is a cross-sectional view illustrating a configuration example of a hydrogen sensor according to Embodiment 3.

FIG. 10 is a cross-sectional view illustrating a configuration example of hydrogen sensor 1 according to Embodiment 3. Hydrogen sensor 1 in FIG. 10 is different from hydrogen sensor 1 in FIG. 1A in that third layer 104c is added in metal oxide layer 104. Hereinafter, different aspects are mainly described, and overlapping descriptions of the same aspects are avoided.

Third layer 104c is in contact with second layer 104b and second electrode 106. The degree of oxygen deficiency of third layer 104c is higher than that of second layer 104b. For example, third layer 104c includes, as the material, TaOx or $Ta_2O_5$ whose degree of oxygen deficiency is higher than that of second layer 104b which includes $Ta_2O_5$ as the material. The degree of oxygen deficiency of third layer 104c is lower than that of first layer 104a.

FIG. 10 illustrates an example of metal oxide layer 104 having a three-layer configuration with first layer 104a that includes TaOx as the material, second layer 104b that includes, as the material, $Ta_2O_5$ whose degree of oxygen deficiency is low, and third layer 104c that includes, as the material, $Ta_2O_5$ whose degree of oxygen deficiency is higher than that of second layer 104b. However, metal oxide layer 104 may have a two-layer configuration with $Ta_2O_5$ whose degree of oxygen deficiency is low and TaOx or $Ta_2O_5$ whose degree of oxygen deficiency is higher than that of the former $Ta_2O_5$.

[3.2 Experimental Data]

Next, operations of hydrogen sensor 1 according to Embodiment 3 are described using experimental data.

Figure 11:
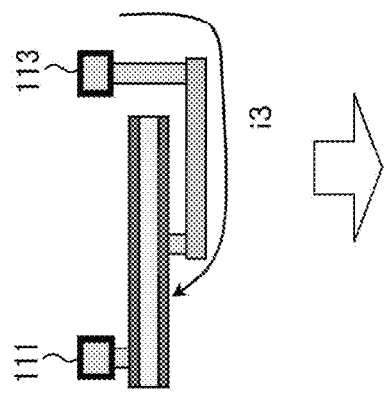
FIG. 11 illustrates an experimental result of a hydrogen sensor of a comparative example.
Figure 11:
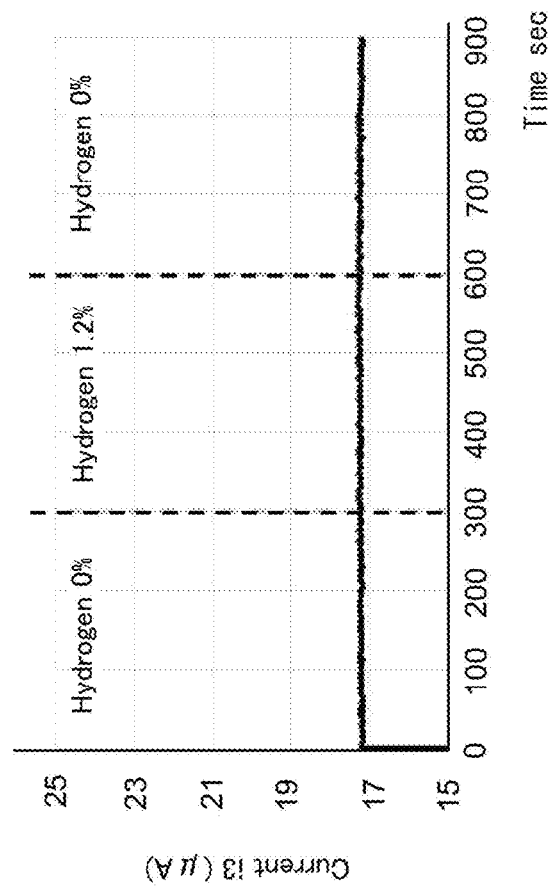

FIG. 11 illustrates experimental data on a hydrogen sensor of a comparative example. Compared to hydrogen sensor 1 according to Embodiment 3, the hydrogen sensor of the comparative example has a configuration which does not include second terminal 112 or the same configuration as hydrogen sensor 1 of Embodiment 3 except that first terminal 111 and second terminal 112 are short-circuited. The measurement conditions in FIG. 11 are the same as those in FIG. 4.

With the hydrogen sensor of the comparative example under the same measurement conditions as those in FIG. 4, current i3 was constant regardless of the presence or absence of hydrogen as illustrated in FIG. 11. In other words, the hydrogen sensor of the comparative example did not react to the gas containing 1.2% of hydrogen and could not detect hydrogen.

Figure 12:
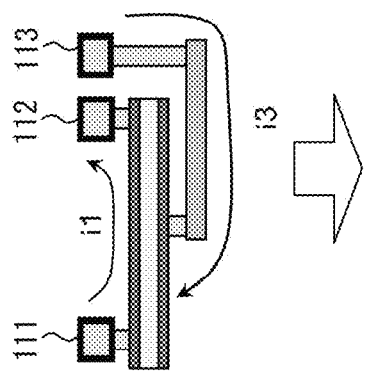
FIG. 12 illustrates an experimental result of the hydrogen sensor according to Embodiment 3.
Figure 12:
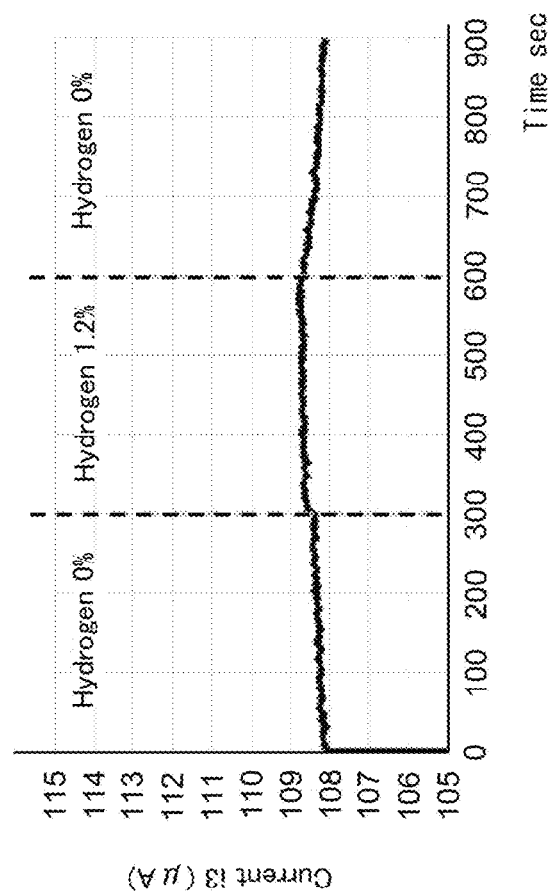

FIG. 12 illustrates an experimental result of hydrogen sensor 1 according to Embodiment 3. The measurement conditions in FIG. 12 are the same as those in FIG. 5.

In hydrogen sensor 1 according to Embodiment 3, current i3 increases in the time period from 300 to 600 in seconds as compared to the other time periods as illustrated in FIG. 12. Furthermore, in the time period from 600 to 900 in seconds, current i3 decreases as compared to the previous time period. According to FIG. 12, current i3 between first terminal 111 and third terminal 113 increases and decreases in response to the presence and absence of hydrogen. Also, in FIG. 12, the response speed in the hydrogen detection is faster than that in FIG. 5.

As described above, metal oxide layer 104 according to Embodiment 3 includes (i) first layer 104a in contact with first electrode 103, (ii) second layer 104b in contact with first layer 104a, and (iii) third layer 104c in contact with second layer 104b and second electrode 106, and third layer 104c has a degree of oxygen deficiency higher than a degree of oxygen deficiency of second layer 104b.

With this, the gas sensitivity of third layer 104c for the hydrogen atoms dissociated by second electrode 106 can be further enhanced.

The degree of oxygen deficiency of third layer 104c may be lower than that of first layer 104a.

Needless to say, the hydrogen detection device and hydrogen detection method illustrated in FIG. 2 and FIG. 3 can be implemented likewise using hydrogen sensors 1 according to Embodiments 2 and 3.

Note that in the example described in each embodiment, second electrode 106 is connected to two terminals, i.e., first terminal 111 and second terminal 112, but the total number of terminals connected to second electrode 106 is not limited to two, and may be three or more. When second electrode 106 has three or more terminals, it is sufficient so long as at least one of the three or more terminals is equivalent to first terminal 111 and at least one of the three or more terminals is equivalent to second terminal 112.

Although the hydrogen sensor, hydrogen detection method, and hydrogen detection device according to one or more aspects have been described based on embodiments, the present disclosure is not limited to such embodiments. Various modifications to the embodiments that are conceivable to those skilled in the art, as well as forms resulting from combinations of constituent elements of different embodiments may be included within the scope of one or more aspects, so long as such modifications and forms do not depart from the essence of the present disclosure.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The hydrogen sensor, hydrogen detection method, and hydrogen detection device according to the present disclosure can be widely used for, for example, detection of leakage of a hydrogen-containing gas.

The invention claimed is:

1. A hydrogen sensor comprising:
a first electrode which is planar;
a second electrode which is planar, faces the first electrode, and includes an exposed portion;
a metal oxide layer which is sandwiched between a surface of the first electrode and a surface of the second electrode facing each other, and has a resistance that changes due to hydrogen; and
two terminals connected to the second electrode.

2. The hydrogen sensor according to claim 1,
wherein the two terminals are positioned with the exposed portion being interposed therebetween in plan view of the second electrode which is planar.

3. The hydrogen sensor according to claim 2,
wherein voltages opposite to each other in polarity are applied to the two terminals as predetermined voltages.

4. The hydrogen sensor according to claim 2,
wherein a resistance between the first electrode and the second electrode changes when gas molecules containing hydrogen atoms come into contact with the exposed portion during passage of a current through the exposed portion.

5. The hydrogen sensor according to claim 2,
wherein a resistance between the two terminals changes when gas molecules containing hydrogen atoms come into contact with the exposed portion during passage of a current through the exposed portion.

6. The hydrogen sensor according to claim 1, comprising:
a local region which is located inside the metal oxide layer, is in contact with the second electrode, and has a degree of oxygen deficiency higher than a degree of oxygen deficiency of the metal oxide layer.

7. The hydrogen sensor according to claim 1, comprising:
a local region which is located inside the metal oxide layer, is in contact with the second electrode, and is a region in which current flows more easily than in the metal oxide layer.

8. The hydrogen sensor according to claim 1, comprising:
a first via which is connected to, of two surfaces of the first electrode, a surface farther from the metal oxide layer, and overlaps with the exposed portion in plan view; and
a connection terminal connected to the first via.

9. The hydrogen sensor according to claim 8,
wherein the two terminals are connected to the second electrode via two second vias connected to the second electrode, and
the first via is located at a central position between the two second vias in the plan view.

10. The hydrogen sensor according to claim 1,
wherein the metal oxide layer includes (i) a first layer in contact with the first electrode and (ii) a second layer in contact with the first layer and the second electrode, and
the second layer has a degree of oxygen deficiency lower than a degree of oxygen deficiency of the first layer.

11. The hydrogen sensor according to claim 1,
wherein the metal oxide layer includes (i) a first layer in contact with the first electrode, (ii) a second layer in contact with the first layer, and (iii) a third layer in contact with the second layer and the second electrode, and
the third layer has a degree of oxygen deficiency higher than a degree of oxygen deficiency of the second layer.

12. A hydrogen detection method in a hydrogen sensor, the hydrogen sensor including:
a first electrode which is planar; a second electrode which is planar, faces the first electrode, and includes an exposed portion; a metal oxide layer which is sandwiched between a surface of the first electrode and a surface of the second electrode facing each other, and has a resistance that changes due to hydrogen; and two terminals connected to the second electrode with the exposed portion being interposed therebetween in plan view of the second electrode which is planar,
the hydrogen detection method comprising:
passing a current through the exposed portion by applying a voltage between the two terminals; and
detecting a gas containing hydrogen atoms by detecting a decrease in a resistance value between the first electrode and the second electrode or by detecting a decrease in a resistance value between the two terminals.

13. A hydrogen detection device comprising:
a first electrode which is planar;
a second electrode which is planar, faces the first electrode, and includes an exposed portion;
a metal oxide layer which is sandwiched between a surface of the first electrode and a surface of the second electrode facing each other, and has a resistance that changes due to hydrogen;
two terminals connected to the second electrode; and
a drive circuit that, in a state of passing a current through the exposed portion by applying a voltage between the two terminals, detects a gas containing hydrogen atoms by detecting a decrease in a resistance value between the first electrode and the second electrode or by detecting a decrease in a resistance value between the two terminals.

* * * * *